United States Patent [19]

Murata et al.

[11] Patent Number: 5,636,921
[45] Date of Patent: Jun. 10, 1997

[54] POWDER DISPERSING APPARATUS WITH MOVABLE POWDER STORING MEMBER

[75] Inventors: Hiroshi Murata; Takeshi Murakami, both of Saitama, Japan

[73] Assignee: Nisshin Flour Milling Co., Ltd., Tokyo, Japan

[21] Appl. No.: 563,567

[22] Filed: Nov. 30, 1995

[51] Int. Cl.$^6$ .................. B01F 13/02; B01F 13/06
[52] U.S. Cl. .................. 366/105; 366/139; 366/191; 366/232; 406/51; 406/52; 406/74; 406/114; 406/115; 406/134; 406/142
[58] Field of Search .................. 366/101, 105, 366/139, 163.1, 191, 220, 221, 232, 240, 349; 406/51, 52, 73, 74, 113, 114, 115, 134, 135, 141–143

[56] References Cited

U.S. PATENT DOCUMENTS

| | | | |
|---|---|---|---|
| 3,951,462 | 4/1976 | De Francisci | 366/191 X |
| 4,497,598 | 2/1985 | Blanton | 406/142 X |

FOREIGN PATENT DOCUMENTS 7035804  2/1995  Japan .

*Primary Examiner*—Charles E. Cooley
*Attorney, Agent, or Firm*—Wesier & Associates, P.C.

[57] ABSTRACT

A powder dispersing apparatus which can disperse every given amount of sample powder in a gas even when the amount is small, thereby continuously generating dispersed powder or floating powder at a desired concentration. The powder dispersing apparatus includes a hollow closed pressure vessel having an air supply port; a suction nozzle mounted to a top portion of the closed pressure vessel and having a cylindrical portion, the suction nozzle being formed with a tubular passage having a suction port at a lower end of the cylindrical portion and a discharge port opening outside the closed pressure vessel; a scraper fixed to the lower end of the cylindrical portion of the suction nozzle so as to be spaced a given distance therefrom, the scraper having a scraper blade located just under the suction port; a powder storing member for storing powder, the powder storing member being rotatable and vertically movable so that the scraper and the cylindrical portion of the suction nozzle are inserted in the powder storing member. The powder storing member may be rotated and vertically moved.

8 Claims, 6 Drawing Sheets

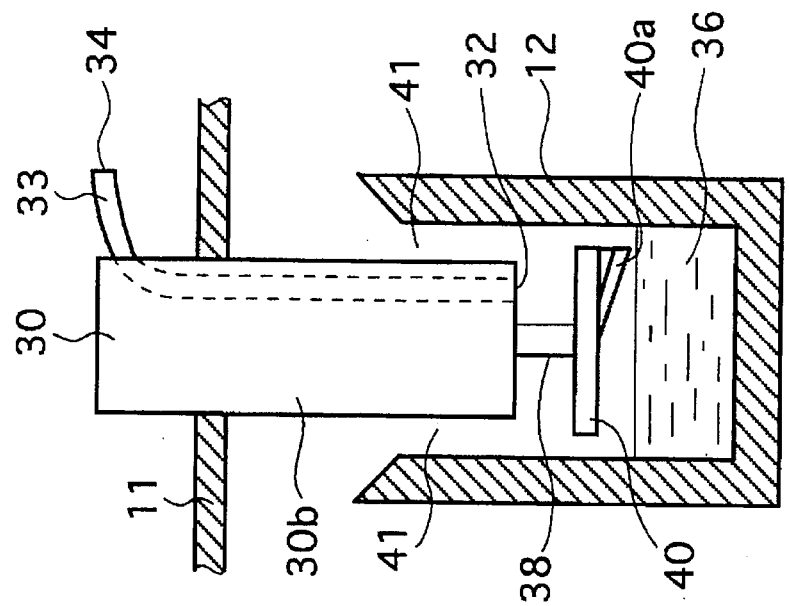
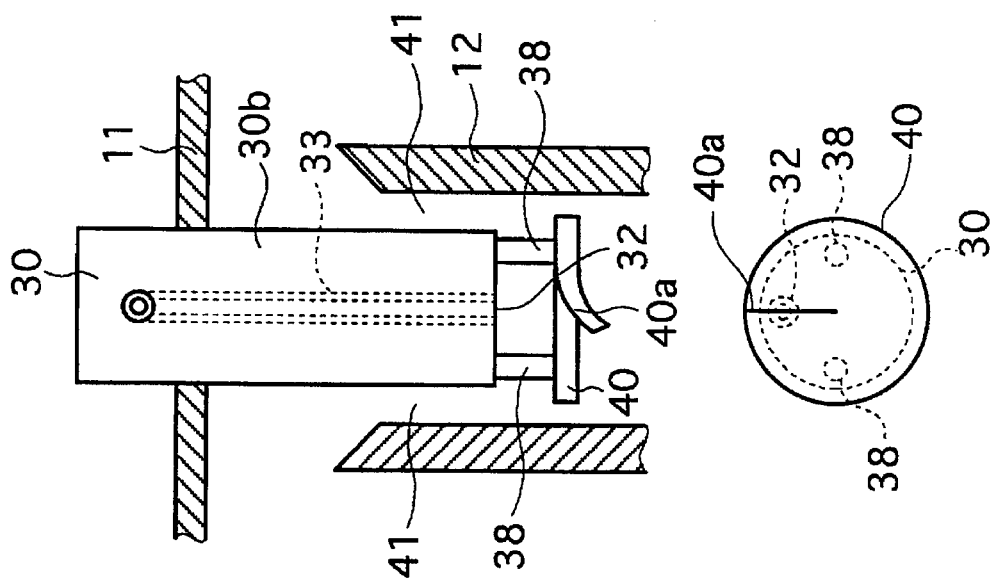
FIG. 2C
FIG. 2A
FIG. 2B

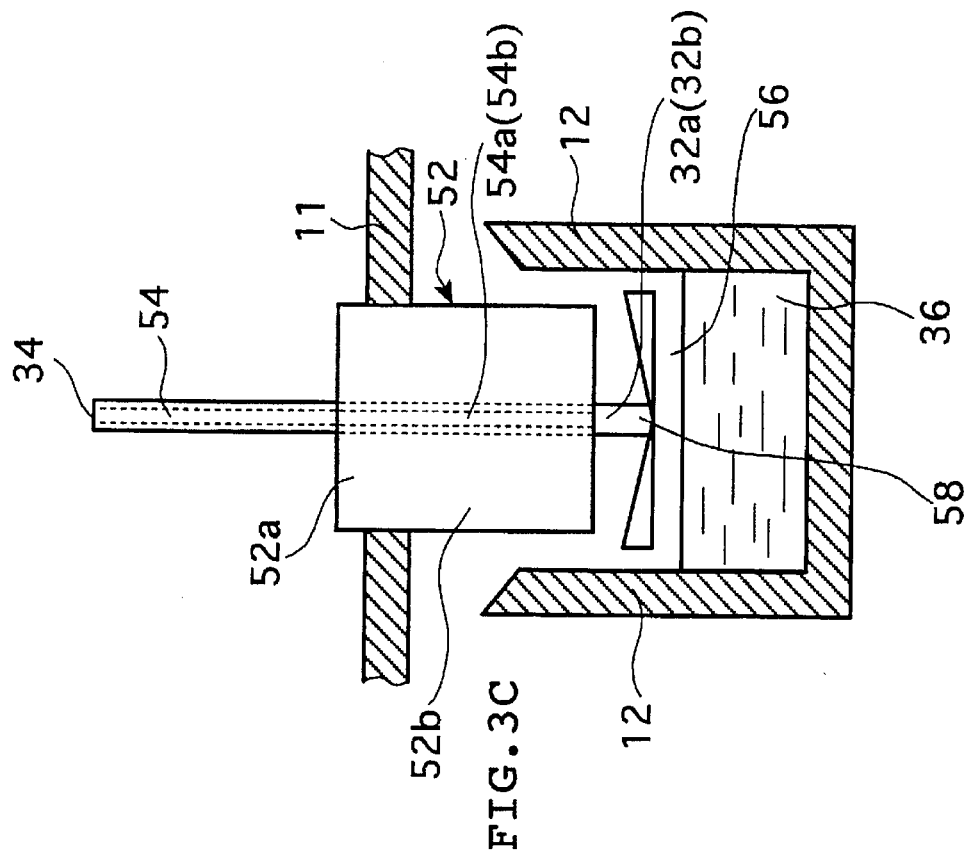
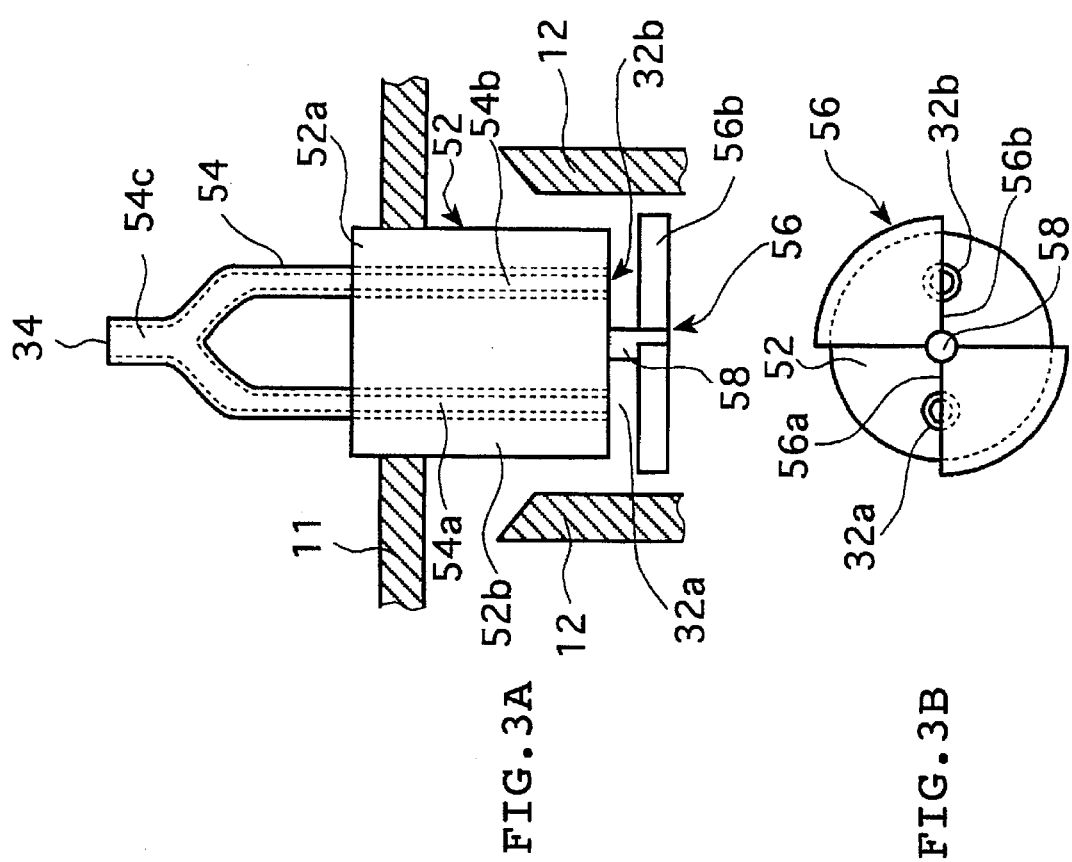

POWDER DISPERSING APPARATUS WITH MOVABLE POWDER STORING MEMBER

BACKGROUND OF THE INVENTION

The present invention relates to a powder dispersing apparatus, and more particularly to a powder dispersing apparatus that can generate floating powder required in examining the properties of powder and supply the floating powder to a powder measuring device or the like.

In recent years, it has been increasingly required to examine not only the macroscopic properties of powder as an aggregate, but also the microscopic properties of powder particles as the characteristics of powder. In examining the microscopic properties of powder particles, it is necessary to measure the particle size, shape, and electric charge, etc. of each powder particle. Conventionally, the powder could be classified according to its particle sizes by using a sieve or the like. In recent years, however, the particle sizes of powder have been greatly inclined to become very small, and the study on powder particles having a particle size of about 1 to 2 µm or less has been increasingly made. It is needless to say that such fine powder cannot be classified by using a sieve.

To measure the particle size of such fine powder without the use of a sieve mesh, a powder measuring device or the like is used to direct a laser beam or any other light beams onto one powder particle and produce a video image by reflection, projection, or photography. Such a powder measuring device requires an apparatus capable of completely isolating the powder particles from each other, i.e., a powder dispersing apparatus. Accordingly, it is greatly desired to provide an apparatus capable of producing floating powder as fine particles and making the concentration thereof constant as one means for completely isolating the powder particles.

To produce such floating powder, a small amount of powder must be dispersed in a large amount of gas. As means for supplying powder to the powder dispersing apparatus, a screw feeder or a vibrating feeder is generally used. However, since the screw feeder and the vibrating feeder are large in size, a large amount of sample powder is required to produce a given amount of floating powder. Conversely, if the size of the feeder is made small, a minimum amount of floating powder such as several grams per hour to several tens of grams per hour required for examination of powder cannot be supplied constantly.

Further, as means for mixing the powder supplied to the powder dispersing apparatus into a given gas flow, an ejector is normally used. However, the ejector causes large pulsation, so that a gas flow with a constant concentration of dispersed powder cannot be generated. Furthermore, since dispersion pressure is also low, the degree of dispersion becomes insufficient.

SUMMARY OF THE INVENTION

It is accordingly an object of the present invention to provide a powder dispersing apparatus which can disperse any given amount of sample powder in a gas even when the amount is small, thereby continuously generating dispersed powder or floating powder at a desired concentration.

The present inventors have already disclosed in Japanese Patent Application No. Hei 5-176734 a device for dispersing powder in a gas by setting the powder in a thin tube and utilizing explosive emission of the gas from one end of the thin tube, as means for generating dispersed powder with a small amount of powder in a batch fashion. This device is greatly useful as in a test of dust explosion that is qualitative and instantaneous. However, this device yet has a problem that powder cannot be fed continuously and quantitatively for a long period of time.

According to the present invention, which achieves the object of the device described in the above Japanese application and solves the problem described above, there is provided a powder dispersing apparatus comprising a hollow closed pressure vessel having an air supply port; a suction nozzle mounted to a top portion of the closed pressure vessel and having a cylindrical portion projecting into the closed pressure vessel, the suction nozzle being formed with a tubular passage having a suction port at a lower end of the cylindrical portion and a discharge port opening outside the closed pressure vessel; a scraper fixed to the lower end of the cylindrical portion of the suction nozzle so as to be spaced a given distance therefrom, the scraper having a scraper blade located just under the suction port; a powder storing member for storing powder, the powder storing member being mounted in the closed pressure vessel so as to be rotatable and vertically movable so that the scraper and the cylindrical portion of the suction nozzle are inserted in the powder storing member with a given space defined between an outer circumferential surface of the cylindrical portion of the suction nozzle and an inner circumferential surface of the powder storing member to form an annular air passage; means for rotating the powder storing member; and means for vertically moving the powder storing member.

The rotating means and the vertically moving means are not necessarily provided in the closed pressure vessel; however, they are preferably provided in the closed pressure vessel to simplify the structure.

Preferably, one pipe forming said tubular passage is embedded in said suction nozzle, or at least two pipes each forming said tubular passage are embedded in said suction nozzle, one end of each pipe opening to said lower end of said cylindrical portion of said suction nozzle to form said suction port, the other ends of all said at least two pipes being joined together to form said discharge port.

According to the present invention, there is a powder dispersing apparatus comprising a hollow closed pressure vessel having an air supply port and a discharge port, a powder storing member provided in said closed pressure vessel for storing powder, a suction nozzle communicating with said discharge port of said closed pressure vessel and inserted in said powder storing member with a given space defined between an outer circumferential surface of said suction nozzle and an inner circumferential surface of said powder storing member to form an annular air passage, an agitator provided so as to be spaced from a lower end of said suction nozzle, means for rotating one of said agitator and said powder storing member relative to each other, and means for vertically moving one of said agitator and said powder storing member relative to each other.

Preferably, said agitator and said suction nozzle are fixed to said closed pressure vessel, and said rotating means and said vertically moving means are stored in said closed pressure vessel to rotate and vertically move said powder storing member.

Preferably, said rotating means and said vertically moving means comprise a nut fixed to a partition board in said closed pressure vessel, a vertically movable ball screw engaged with internal threads of said nut, a motor for rotating said ball screw, a rotation stop to which said motor is fixed, and a motor guide fixed to an inner wall surface of said closed pressure vessel so as to extend in parallel to an axis of said ball screw, for vertically slidably engaging said rotation stop, whereby said motor is driven to rotate and vertically move said powder storing member fixed to an upper end of said ball screw, or said vertically moving means comprises a vertical movement motor fixed to a partition board in said closed pressure vessel, a ball screw adapted to be rotated by said vertical movement motor, a vertically movable member having an internal thread portion engaged with said ball screw, and a linear bearing fixed to an inner wall surface of said closed pressure vessel for vertically movably supporting said vertically movable member; and said rotating means comprises a rotation motor fixed to said vertically movable member, and a rotating shaft adapted to be rotated by said rotation motor and having an upper end fixed to said powder storing member.

Other objects and features of the invention will be more fully understood from the following detailed description and appended claims when taken with the accompanying drawings.

BRIEF DESCRIPTION OF THE DRAWINGS

FIGS. 2A, 2B, and 2C are a sectional front view, a bottom plan view, and a sectional side view, respectively, showing the details of an essential part of the powder dispersing apparatus shown in FIG. 1;

FIGS. 3A, 3B, and 3C are a sectional front view, a bottom plan view, and a sectional side view, respectively, showing the details of an essential part of a modification of the powder dispersing apparatus according to the present invention.

DETAILED DESCRIPTION OF THE INVENTION

The present invention is described below in detail.

The powder dispersing apparatus of the present invention is designed to generate a constant concentration of floating powder with a high degree of dispersion, e.g., in a completely isolated condition of powder particles, as required in examining the microscopic properties of sample powder. More specifically, the powder dispersing apparatus of the present invention is designed to scrape up and float a small amount of sample powder stored in a powder storing member with a scraper blade of a scraper, suck the floating powder from a suction port of a suction nozzle into a tubular passage formed in the suction nozzle by using compressed air supplied from an air supply port into a closed pressure vessel and passed through an air passage defined between the suction nozzle and the powder storing member, disperse the floating powder in the compressed air flowing in the tubular passage, and discharge the dispersed powder from a discharge port to the outside of the closed pressure vessel, that is, the outside of the powder dispersing apparatus. A powder measuring device or the like is connected to the discharge port of the powder dispersing apparatus.

In the powder dispersing apparatus of the present invention, the sample powder is stored in the powder storing member. In this condition, the powder storing member is rotated and raised by the rotating means and the vertically moving means. At the same time, the dry compressed air is supplied from the air supply port of the closed pressure vessel. That is, the powder storing member is rotated and raised by the rotating means and the vertically moving means to thereby make the scraper scrape up and float the sample powder stored in the powder storing member. At the same time, the dry compressed air is supplied from the air supply port of the closed pressure vessel to produce a pressure difference between the pressure inside the closed pressure vessel and the pressure inside a powder measuring device or the like connected to the discharge port of the powder dispersing apparatus. Owing to this pressure difference, the dry compressed air is passed through the air passage defined between the outer wall surface of the suction nozzle and the inner wall surface of the powder storing member to reach the suction port of the suction nozzle. At this time, the powder scraped up to float directly under the suction port is carried by the dry compressed air and is sucked into the suction port together with the dry compressed air. Then, the powder air mixture (floating powder) is dispersed in the tubular passage of the suction nozzle during conveyance to the discharge port. Then, the dispersed powder is discharged from the discharge port to the outside of the powder dispersing apparatus and is supplied to the powder measuring device or the like.

In another aspect of the present invention, an agitator is used in place of the scraper to agitate and float the sample powder. The floating powder is dispersed and carried by the compressed air to be fed from the suction port to the discharge port, then being discharged therefrom to the outside of the closed pressure vessel. In this case, the rotating means and the vertically moving means are not especially limitative provided that the former can rotate one of the agitator and the powder storing member relative to each other and the latter can vertically move one of the agitator and the powder storing member relative to each other to bring them close to each other. For example, the agitator may be rotated and lowered, or the powder storing member may be rotated and raised. Otherwise, one of them may be rotated and the other may be vertically moved.

That is, the rotating means in the present invention is designed to rotate the powder storing member or the scraper (or the agitator), thereby making the scraper (or the agitator) scrape (or agitate) and float the powder stored in the powder storing member toward the suction port. Further, the vertically moving means in the present invention is designed to raise the powder storing member or vertically move one of the powder storing member and the scraper (or the agitator) relative to each other, thereby bringing the powder stored in the powder storing member and the scraper (or the agitator) into contact with each other. In a preferred embodiment of the present invention, a screw type elevating device capable of simultaneously rotate and raise the powder storing member is conveniently used as the rotating means and the vertically moving means.

According to the powder dispersing apparatus of the present invention, even a small amount of sample powder can be scraped or agitated to float, and such floating powder can be sucked from the suction port. Further, since the floating powder is fed by the pressure difference, the dispersibility of the powder in the pipe can be greatly improved to thereby obtain completely isolated powder particles, for example. According to the powder dispersing apparatus of the present invention, the powder can be dispersed always at a constant concentration because of no possibility of pulsation. Further, the concentration of the scraped powder (floating powder) can be freely set by changing the moving speed of the powder storing member and/or by adjusting the space between the suction nozzle and the scraper or the agitator. According to the powder dispersing apparatus of the present invention, the floating powder can be generated simply by supplying the dry compressed air into the closed pressure vessel and relatively rotating and raising the powder storing member in which the powder is stored by operating the rotating means and the vertically moving means, thus improving the operability. Moreover, since the powder hardly remains in the closed pressure vessel, especially in the powder storing member after operation, it is unnecessary to wash the interior of the powder dispersing apparatus after operation, thus improving the maintainability. The scraping amount of the powder, that is, the concentration of the dispersed powder is greatly affected by the relative rising speed of the powder storing member. Accordingly, means for raising the powder storing member and means for rotating it may be separately provided to select proper values of the operating speeds of both means.

On the pages that follow, the powder dispersing apparatus of the present invention is described in detail with reference to the preferred embodiments shown in accompanying drawings.

Figure 1:
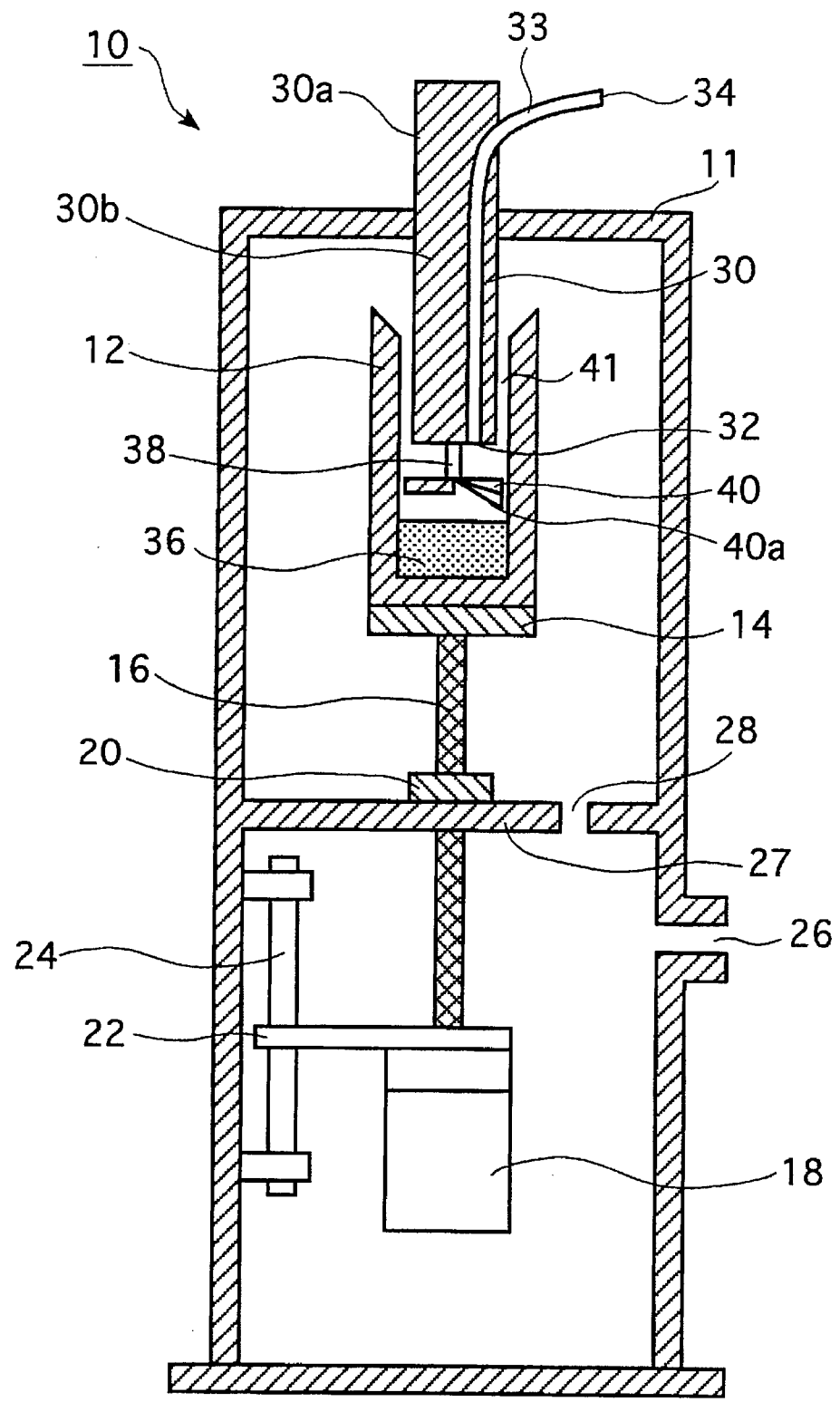
FIG. 1 is a sectional side view of a powder dispersing apparatus according to a preferred embodiment of the present invention.

FIG. 1 is a sectional side view of a powder dispersing apparatus 10 according to a first preferred embodiment of the present invention. The powder dispersing apparatus 10 has a suction nozzle 30, a scraper 40, a cylinder 12 as the powder storing member in the present invention, means for rotating and vertically moving the cylinder 12, and a closed pressure vessel 11 for accommodating these members except a part of the suction nozzle 30. An air supply port 26 for supplying dry compressed air into the closed pressure vessel 11 is formed through a side wall of a lower portion of the closed pressure vessel 11. A pipe 33 having a discharge port 34 connected to a powder measuring device (not shown) or the like is embedded in the suction nozzle 30, and a part of the suction nozzle 30 projects out of the closed pressure vessel 11 at its upper end portion. The interior of the closed pressure vessel 11 is divided into two, upper and lower spaces by a partition board 27 having a through hole 28 near the vertical center of the closed pressure vessel 11.

The suction nozzle 30 is hermetically mounted to the upper end portion of the closed pressure vessel 11. One end portion (upper end portion) 30a of the suction nozzle 30 projects out of the closed pressure vessel 11 at its upper end portion, and the other end portion (lower end portion) 30b of the suction nozzle 30 having a cylindrical shape projects into the closed pressure vessel 11 at its upper end portion. The pipe 33 forming a tubular passage for passing a powder air mixture is embedded in the suction nozzle 30. The pipe 33 has a suction port 32 at one end thereof opening into the closed pressure vessel 11 at the bottom of the lower end portion 30b of the suction nozzle 30. The other end of the pipe 33 projects from the side surface of the upper end portion 30a of the suction nozzle 30, and is formed as the discharge port 34 opening to the outside of the closed pressure vessel 11.

The scraper 40 is mounted to the bottom of the lower end portion 30b of the suction nozzle 30 with a given space defined therebetween by two support rods 38 (see FIG. 2A). As specifically shown in FIGS. 2A, 2B, and 2C, the scraper 40 is a disk slightly larger in diameter than the cylindrical lower end portion 30b of the suction nozzle 30. The scraper 40 has a cut extending from the center to the circumference of the disk. That is, the cut corresponds to the radius of the disk. One of adjacent cut portions of the disk separated along the cut is slightly bent downward to form a scraper blade 40a for scraping powder 36. The scraper blade 40a is located just under the suction port 32. Preferably, the distance between the lower end portion 30b of the suction nozzle 30 and the scraper 40 is adjustable according to the kind of the powder 36.

The cylinder 12 has an open top and a closed bottom to store the powder 36. The cylinder 12 has an inner diameter slightly larger than the diameter of the scraper 40. The scraper 40 and the cylindrical lower end portion 30b of the suction nozzle 30 are received into the cylinder 12 from the open top thereof. The cylinder 12 is rotatable and vertically movable. The annular space defined between the inner circumferential surface of the cylinder 12 and the outer circumferential surface of the cylindrical lower end portion 30b of the suction nozzle 30 functions as an air passage 41 for passing the compressed air supplied into the closed pressure vessel 11.

In the powder dispersing apparatus 10 according to this preferred embodiment, the upper surface of the powder 36, especially, fine powder, is scraped up or off by the scraper blade 40a of the scraper 40. At the same time, the powder 36 thus scraped is introduced into the pipe 33 as a thin tube by the air flowing around the scraper 40, and is then dispersed in the air conveyed in the pipe 33. Accordingly, sufficiently dispersed powder particles, e.g., mono-dispersed particles, can be obtained.

The scraper blade **40*a* functions to scrape the upper surface of the powder 36, float a given amount of particles of the powder 36, and introduce the particles carried by the compressed air to the suction port 32 located directly over the scraper blade 40*a*. That is, the scraper blade 40*a* functions to not only make constant an amount of powder particles to be scraped, but also straighten the flow of the compressed air to be introduced. As shown in FIGS. 2A, 2B, and 2C, the diameter of the scraper 40 is set slightly larger than the diameter of the cylindrical lower end portion 30*b* of the suction nozzle 30. This setting is due to the following reason. While the air passage 41 must be formed between the suction nozzle 30 and the cylinder 12, the powder 36 is not dispersed by stirring and mixing in the cylinder 12, so that a so large dispersion space is not required in the cylinder 12. Accordingly, the space between the scraper 40 and the upper surface of the powder 36** is not required to be used as a dispersion space, but it is preferable to straighten the flow of the compressed air to be introduced.

Accordingly, the shape and the size of the scraper 40 and the scraper blade **40*a* are not particularly limitative, but they may be suitably selected according to the kind of the powder 36, the density of dispersed powder particles to be required, the rotating speed of the cylinder 12, the amount of the dry compressed air to be introduced, etc. Preferably, the scraper blade 40*a* is mounted or formed on a disk or the like because the upper surface of the powder 36** in the cylinder is rotated.

In the present invention, the suction port 32 of the suction nozzle 30 must be located just over the scraper blade **40*a* of the scraper 40. This is due to the reason that a given amount of powder 36 scraped by the scraper blade 40*a* must be well carried by the compressed air to be sucked into the suction port 32. The tubular passage extending between the suction port 32 and the exhaust port 34 located outside the closed pressure vessel 11 is formed by the pipe 33, and functions to accelerate dispersion and mixing of the powder 36 in the compressed air conveyed to the discharge port 34. Accordingly, the length and the diameter of the pipe 33** are not particularly limitative, but it is preferable that they may be suitably set according to the degree of dispersion of the powder to be required, the conveyance conditions of the pipe 33, etc.

While the single tubular passage for acceleration of powder dispersion is formed in the suction nozzle 30 in the above preferred embodiment shown in FIGS. 1 and 2A to 2C, a plurality of tubular passages may be formed in the suction nozzle 30, and the number of such tubular passages is not limitative in the present invention. In the case that a plurality of tubular passages are formed in the suction nozzle 30, it is preferable that a plurality of scraper blades of a scraper are respectively provided for a plurality of suction ports of the plural tubular passages. While the plural tubular passages may respectively have a plurality of discharge ports, it is preferable that at least two or all of the plural tubular passages are joined together in the midway to thereby reduce the number of the discharge ports or make them one discharge port.

FIGS. 3A, 3B, and 3C are a sectional front view, a bottom plan view, and a sectional side view of another preferred embodiment of the suction nozzle and the scraper, in which two tubular passages are formed in the suction nozzle. As shown in FIGS. 3A to 3C, two pipes 54a and 54b forming the two tubular passages are embedded in a suction nozzle 52. The lower ends of the two pipes 54a and 54b open to the bottom of a lower end portion 52b of the suction nozzle 52 to form two suction ports 32a and 32b, respectively. The upper ends of the two pipes 54a and 54b project from the top of an upper end portion 52a of the suction nozzle 52, and are joined together outside the closed pressure vessel 11 to form one pipe 54c. The upper open end of the pipe 54c forms one discharge port 34. Thus, a joined pipe 54 having the two suction ports 32a and 32b and the one discharge port 34 is formed.

A scraper 56 spaced a given distance from the bottom of the suction nozzle 52 is mounted at the center of the bottom of the suction nozzle 52 by a single support rod 58. The scraper 56 has such a shape as by cutting off two quarter parts of a disk in a symmetrical fashion with respect to the center of the disk, and arranging the remaining two quarter parts of the disk so that the aligned two radii of the two quarter parts are located just under the suction ports 32a and 32b, respectively. The thickness of each quarter part forming the scraper 56 is gradually increased from the radius located just under the suction port 32a or 32b to the other radius, thus forming two scraper blades 56a and 56b.

The suction nozzle having the plural tubular passages can be constructed as mentioned above.

With this construction, the flow of compressed air is introduced along the outer wall surface of the suction nozzle to the pipe. Accordingly, the powder scraped by the scraper blades is immediately sucked into the nozzle and is less scattered to any portions other than the nozzle. Therefore, means for driving the cylinder can be accommodated in the closed pressure vessel with less mechanical problem.

Referring back to FIG. 1, the cylinder 12 is fixed to the upper surface of a rotating table 14. The rotating table 14 is rotated and vertically moved to thereby rotate and vertically move the cylinder 12. The means for rotating and vertically moving the cylinder 12 includes the rotating table 14 on which the cylinder 12 is fixedly placed, a motor guide 24 fixed to the inner wall surface of the closed pressure vessel 11 so as to extend vertically in parallel thereto, a rotation/vertical movement motor (which will be hereinafter referred to simply as a motor) 18 mounted through a plate-like rotation stop 22 to the motor guide 24 so as to be vertically movable along the motor guide 24 and be prevented from horizontally rotating by the rotation stop 22, a ball screw 16 directly connected at its lower end to the output shaft of the motor 18 and thereby adapted to be rotated by the motor 18, the upper end of the ball screw 16 being connected to the rotating table 14, and a nut 20 fixed to the partition board 27 formed at the vertically central portion of the closed pressure vessel 11 and having internal threads engaged with the ball screw 16.

While the suction nozzle 30 in which the pipe 33 having the suction port 32 and the discharge port 34 is embedded is hermetically mounted to the top portion of the closed pressure vessel 11 in the condition where the scraper 40 is fixed to the suction nozzle 30, it is preferable that the suction nozzle 30 is removably mounted to the top portion of the closed pressure vessel 11. For example, the suction nozzle 30 may be made removable from the closed pressure vessel 11 by forming threads (not shown) on both the suction nozzle 30 and the top portion of the closed pressure vessel 11 (for example, by forming external threads on the outer circumference of the suction nozzle 30 and internal threads through the top portion of the closed pressure vessel 11), and fixedly engaging the threads of both the suction nozzle 30 and the top portion of the closed pressure vessel 11. Any other means for hermetically mounting the suction nozzle 30 to the closed pressure vessel 11 may be adopted, or known mounting means may be also be adopted. With this arrangement that the suction nozzle 30 with the scraper 40 fixed thereto is removable from the closed pressure vessel 11, the powder 36 can be easily stored into the cylinder 12.

While the rotating and vertically moving means for the cylinder 12 inclusive of its driving section is stored in the closed pressure vessel 11, the driving section may be located outside the closed pressure vessel 11. Further, the mechanism for vertically moving the cylinder 12 may be driven by fluid pressure such as oil pressure or air pressure.

In using the powder dispersing apparatus 10 according to this preferred embodiment, the suction nozzle 30 with the scraper 40 is removed from the closed pressure vessel 11, and the cylinder 12 is taken out of the closed pressure vessel 11. After storing the sample powder 36 into the cylinder 12, the cylinder 12 is fixed to the rotating table 14. Then, the suction nozzle 30 with the scraper 40 is again hermetically mounted to the closed pressure vessel 11. Thereafter, a compressed air source (not shown) for supplying dry compressed air is connected to the air supply port 26 of the closed pressure vessel 11, and a powder measuring device (not shown) or the like is connected to the discharge port 34 of the pipe 33 projecting out of the closed pressure vessel 11. In this condition, the motor 18 is operated to rotate the ball screw 16, and the dry compressed air is supplied from the air supply port 26 of the closed pressure vessel 11. Thus, the scraper blade 40a of the scraper 40 is inserted in the powder 36 stored in the cylinder 12 rotationally driven to thereby scrape the upper surface portion of the powder 36 and float it. The floating powder 36 is sucked from the suction port 32 of the suction nozzle 30 together with the compressed air passing the air passage 41 defined between the cylindrical lower end portion 30b of the suction nozzle 30 and the cylinder 12. The powder 36 sucked into the pipe 33 is dispersed in the compressed air flowing in the pipe 33, thereby obtaining a sufficiently dispersed condition of the powder 36, e.g., mono-dispersed powder particles, which are in turn exhausted from the exhaust port 34 of the pipe 33 to the outside of the closed pressure vessel 11 of the powder dispersing apparatus 10, then being supplied to the powder measuring device or the like.

The motor 18 is mounted through the rotation stop 22 to the vertically extending motor guide 24 fixed to the inner wall surface of the closed pressure vessel 11 so as to be vertically movable along the motor guide 24 and be prevented from horizontally rotating by the rotation stop 22. Accordingly, when the motor 18 is operated, the ball screw 16 directly connected to the output shaft of the motor 18 is rotated. The rotation of the ball screw 16 by the motor 18 causes rotation of the cylinder 12 fixedly placed on the rotating table 14 mounted to the upper end of the ball screw 16. Further, the ball screw 16 is engaged with and supported to the internal threads of the nut 20 fixed to the partition board 27 formed at the central portion of the closed pressure vessel 11. Accordingly, the ball screw 16, the motor 18, and the cylinder 12 are raised together with respect to the nut 20 per revolution of the ball screw 16 according to the pitch of the ball screw 16.

On the other hand, the dry compressed air supplied from the air supply port 26 of the closed pressure vessel 11 is passed through the through hole 28 of the partition board 27 of the closed pressure vessel 11 and through the air passage 41 defined between the outer wall surface (outer circumferential surface) of the cylindrical lower end portion 30b of the suction nozzle 30 and the inner wall surface (inner circumferential surface) of the cylinder 12 to reach the powder 36 stored in the cylinder 12, by a pressure difference between the pressure inside the closed pressure vessel 11 and the pressure outside the closed pressure vessel 11, e.g., the pressure inside the powder measuring device or the like connected to the discharge port 34 of the pipe 33 projecting from the closed pressure vessel 11. Since the cylinder 12 is rotated and raised as mentioned above, the powder 36 is scraped up to be floated by the scraper blade 40a of the scraper 40. Then, the floating powder 36 is sucked into the suction port 32 of the suction nozzle 30 located just over the scraper blade 40a together with or as being carried by the dry compressed air having reached the suction port 32. Thereafter, the powder 36 and the compressed air are conveyed under pressure in the tubular passage of the pipe 33 in the suction nozzle 30, and dispersion and mixing of the powder 36 in the compressed air are repeated during conveyance in the tubular passage. Finally, the dispersed powder 36 in the compressed air is discharged from the discharge port 34 of the pipe 33, and is supplied to the powder measuring device or the like.

In this manner, the cylinder 12 fixedly placed on the rotating table 14 mounted to the upper end of the ball screw 16 is rotated at a high speed, and is simultaneously raised at a low speed according to the pitch of the ball screw 16, thereby making the scraper 40 scrape up and float the powder 36. At the same time, the dry compressed air is supplied from the air supply port 26 of the closed pressure vessel 11 to thereby produce a pressure difference between the pressure inside the closed pressure vessel 11 and the pressure inside the powder measuring device or the like connected to the discharge port 34 of the closed pressure vessel 11. Owing to this pressure difference, the powder 36 scraped up by the scraper 40 is sucked into the pipe 33 in the suction nozzle 30 together with the dry compressed air to thereby disperse and mix the powder 36 in the compressed air sucked into the pipe 33. Then, the dispersed powder 36 in the compressed air flowing in the pipe 33 is supplied through the discharge port 34 to the powder measuring device or the like. While the air is used as a medium for dispersing the powder 36 in this preferred embodiment, the dispersion medium in the present invention is not limited to air, but any gas having no influence upon the powder may be used. For example, an inert gas such as nitrogen gas or argon gas may be used.

In the powder dispersing apparatus 10 according to this preferred embodiment, the motor 18, the ball screw 16, and the cylinder 12 may be returned to an original position (rise starting position) after raising the cylinder 12 by a given distance, by reversely driving the motor 18 to reversely rotate the ball screw 16. Further, in the powder dispersing apparatus 10 according to this preferred embodiment, all the components are enclosed in the closed pressure vessel 11 to reduce the space occupied by the powder dispersing apparatus 10 and make the structure as simple as possible. To this end, the rotating means and the vertically moving means for the cylinder 12 are preferably constructed from the single motor 18 as mentioned above.

The powder dispersing apparatus 10 according to this preferred embodiment is basically constructed as mentioned above.

Figure 4:
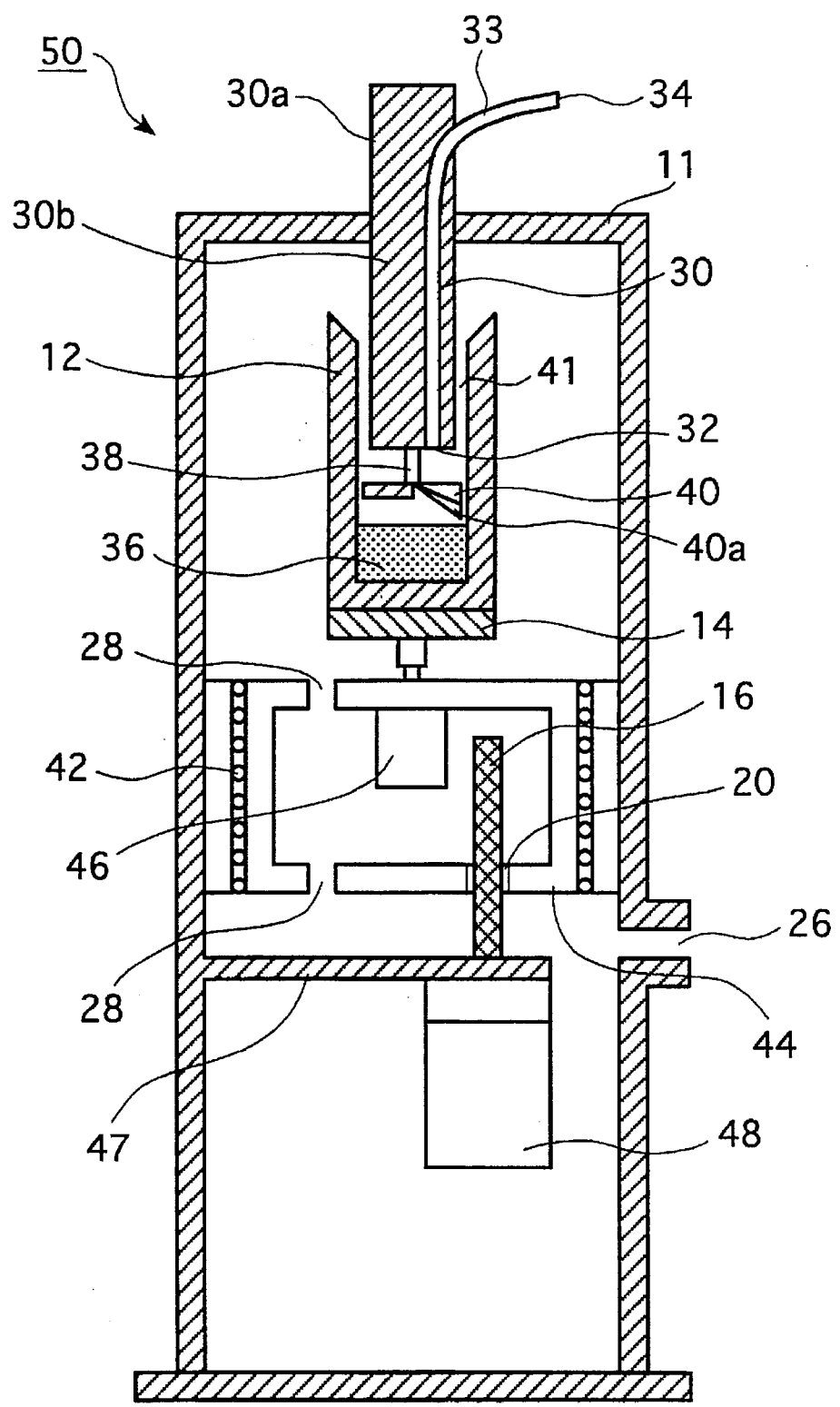
FIGS. 4, 5, and 6 are sectional side views of other preferred embodiments of the powder dispersing apparatus according to the present invention.

FIG. 4 is a sectional side view of a powder dispersing apparatus 50 according to a second preferred embodiment of the present invention. The powder dispersing apparatus 50 shown in FIG. 4 is different from the powder dispersing apparatus 10 shown in FIG. 1 in the points that the partition board 27 having the through hole 28 and supporting the nut 20 is not formed at the central portion of the closed pressure vessel 11 and that the rotating means and the vertically moving means for the cylinder 12 are different. The other parts are the same as those in FIG. 1, so that these same parts will be denoted by the same reference numerals and the description thereof will be omitted hereinafter.

In the powder dispersing apparatus 50 shown in FIG. 4, the rotating means and the vertically moving means in the present invention include a liner bearing 42 formed on the inner wall surface of a closed pressure vessel 11 so as to extend vertically, a vertically movable member 44 mounted to the linear bearing 42 so as to be vertically movable along the liner bearing 42 and horizontally unrotatable (e.g., by making the horizontal sectional shape of the vertically movable member 44 not circular such as rectangular), and having through holes 28 and a nut 20 formed with internal threads, a rotation motor 46 fixed to the vertically movable member 44 and having a rotating shaft mounted at its upper end to a rotating table 14 on which a cylinder 12 is fixedly placed, and a vertical movement motor 48 fixed to a support plate 47 extending horizontally from the inner wall surface of the closed pressure vessel 11 and having a rotating shaft directly connected to a ball screw 16 engaged with and support to the internal threads of the nut 20 of the vertically movable member 44, thereby vertically moving the vertically moving member 44.

As mentioned above, the vertically movable member 44 is mounted to the vertically extending linear bearing 42 formed on the inner wall surface of the closed pressure vessel 11 in such a manner that the vertically movable member 44 is vertically movable along the linear bearing 42 and is horizontally unrotatable. Further, the rotation motor 46 is fixed to the vertically movable member 44. Accordingly, when the rotation motor 46 is operated, the cylinder 12 fixedly placed on the rotating table 14 is rotated by the rotation motor 46. On the other hand, the vertical movement motor 48 is fixed to the support plate 47 extending horizontally from the inner wall surface of the closed pressure vessel 11, and the ball screw 16 directly connected to the rotating shaft of the vertical movement motor 48 is engaged with and supported to the internal threads of the nut 20 of the vertically movable member 44. Accordingly, when the vertical movement motor 48 is operated, the vertically movable member 44, the rotation motor 46, and the cylinder 12 are raised together per revolution of the ball screw 16 according to the pitch of the ball screw 16.

On the other hand, the dry compressed air supplied from an air supply port 26 of the closed pressure vessel 11 is passed through the through holes 28 of the vertically movable member 44 and through an air passage 41 defined between the outer wall surface of the suction nozzle 30 and the inner wall surface of the cylinder 12 to reach powder 36 stored in the cylinder 12, owing to a pressure difference between the pressure inside the closed pressure vessel 11 and the pressure inside a powder measuring device (not shown) or the like connected to a discharge port 34 opening to the outside of the closed pressure vessel 11. Since the cylinder 12 is rotated and raised by the motors 46 and 48 as mentioned above, the powder 36 is scraped up and floated by a scraper blade 40a of a scraper 40 mounted through a support rod 38 to the bottom of the suction nozzle 30. The floating powder 36 is then carried by the dry compressed air having reached a suction port 32 of the suction nozzle 30 located just over the scraper blade 40a, and is sucked into the suction port 32 together with the dry compressed air. Then, the powder air mixture is conveyed in a tubular passage of a pipe 33 embedded in the suction nozzle 30, and is discharged from the discharge port 34 outside the closed pressure vessel 11, thereafter being supplied to the powder measuring device or the like.

In this manner, the cylinder 12 fixedly placed on the rotating table 14 fixed to the upper end of the rotating shaft of the rotation motor 46 is rotated at a high speed by operating the rotation motor 46, and is simultaneously raised at a low speed by operating the vertical movement motor 48 to rotate the ball screw 16, thereby making the scraper 40 scrape up and float the powder 36. At the same time, the dry compressed air is supplied from the air supply port 26 of the closed pressure vessel 11 to produce a pressure difference between the pressure inside the closed pressure vessel 11 and the pressure inside the powder measuring device or the like. This pressure difference makes suction of the floating powder 36 and the dry compressed air into the suction port 32, and the powder 36 thus sucked is sufficiently dispersed in the compressed air during conveyance through the pipe 33. Then, the sufficiently dispersed powder 36, e.g., monodispersed powder particles, is supplied through the discharge port 34 to the powder measuring device or the like.

In the powder dispersing apparatus 50 according to this preferred embodiment, after raising the cylinder 12 by a given distance, the vertically movable member 44, the rotation motor 46, and the cylinder 12 can be returned to an original vertical position by reversely driving the vertical movement motor 48. Further, the powder dispersing apparatus 50 according to this preferred embodiment is suitably used in the case that the space occupied by the powder dispersing apparatus 50 is allowed to be relatively large, and so it is preferable that the rotating means and the vertically moving means in the present invention are independently constructed by the rotation motor 46 and the vertical movement motor 48, respectively, as mentioned above. With this arrangement, the motor can be divided into a high-rotation motor and a high-torque motor, thereby reducing the cost of the motor. That is, the cylinder 12 is rotated at a high speed by the rotation motor 46, and is vertically moved at a low speed by the vertical movement motor 48, thereby obtaining arbitrary optimum rotating speed and vertically moving speed.

The powder dispersing apparatus of the present invention is not limited to the above preferred embodiments shown in FIGS. 1 to 4, but may be applied to other preferred embodiments as shown in FIGS. 5 and 6, in which the suction nozzle 30 and the scraper 40 fixed thereto through the support rod or rods 38 are replaced by a suction nozzle 62 and an agitator 70 fixed thereto through a support rod 68. FIGS. 5 and 6 show powder dispersing apparatuses 60 and 80 identical with the powder dispersing apparatuses 10 and 50, respectively, except the above point. Therefore, the same parts as those shown in FIGS. 1 to 4 will be denoted by the same reference numerals, and the description thereof will be omitted hereinafter.

In the powder dispersing apparatuses 60 and 80 shown in FIGS. 5 and 6, respectively, a discharge port 66 is formed on the side surface of an upper end portion of a closed pressure vessel 11, and a powder dispersing air passage is formed so as to extend from the discharge port 66 into the closed pressure vessel 11. A hollow suction nozzle 62 is fixed at its upper end to the closed pressure vessel 11 and having a suction port 64 at the lower end communicating with the powder dispersing air passage. A support rod 68 is inserted into the suction nozzle 62 from the suction port 64. The upper end of the support rod 68 is fixed to the upper end portion of the suction nozzle 62 exposed to the discharge port 66, and the lower end of the support rod 68 projects from the suction port 62. A screw 70 as the agitator in the present invention is fixed to the lower end of the support rod 68 projecting from the suction port 64 of the suction nozzle 62.

In using the powder dispersing apparatus 60 or 80, a cover (not shown) of the closed pressure vessel 11 is removed with the suction nozzle 62, the screw 70, and the support rod 68 from the closed pressure vessel 11. Then, sample powder 36 is stored into the cylinder 12, and the cover is mounted again to the closed pressure vessel 11. Next, a compressed air source (not shown) for supplying dry compressed air into the closed pressure vessel 11 is connected to an air supply port 26 of the closed pressure vessel 11, and a powder measuring device (not shown) or the like is connected to the discharge port 66 of the closed pressure vessel 11. In this condition, a motor 18 or motors 46 and 48 is or are operated to rotate the ball screw 16 and thereby rotate and raise the cylinder 12. Simultaneously, the dry compressed air is supplied from the air supply port 26 into the closed pressure vessel 11. Accordingly, the screw 70 is inserted into the powder 36 stored in the cylinder 12 to thereby agitate and float the powder 36. The floating powder 36 is carried by the dry compressed air introduced into the cylinder 12. Thus, the floating powder 36 is dispersed and mixed in the dry compressed air to obtain a powder air mixture, which is in turn sucked into the suction port 64 of the suction nozzle 62 and flows in the air passage formed in the suction nozzle 62 to reach the discharge port 66, thereafter being supplied to the powder measuring device or the like provided outside the powder dispersing apparatus 60 or 80.

While the powder dispersing apparatuses 10 and 50 shown in FIGS. 1 to 4 are superior in stability to the powder dispersing apparatuses 60 and 80 shown in FIGS. 5 and 6, all the powder dispersing apparatuses 10, 50, 60, and 80 according to the present invention can exhibit such effects that the powder can be dispersed at a given concentration and the concentration can be freely set.

The present invention will be more clearly understood with reference to the following examples.

EXAMPLE 1

As shown in FIG. 1, the powder 36 was put into the cylinder 12 having an inner diameter of 22 mm and a depth of 60 mm. The powder 36 in the cylinder 12 was pressed so that the height of the powder 36 from the inner bottom surface of the cylinder 12 became 15 to 30 mm. Then, the cylinder 12 was fixedly placed on the rotating table 14 set in the closed pressure vessel 11. The rotating table 14 was connected to the motor 18 through the ball screw 16 having a diameter of 10 mm, a screw thread pitch of 1 mm, and a length of 90 mm. The ball screw 16 was engaged with the internal threads of the nut 20 fixed to the partition board 27 in the closed pressure vessel 11. The motor 18 was vertically movably mounted through the rotation stop 22 to the motor guide 24 mounted in parallel to the inner wall surface of the closed pressure vessel 11. When the motor 18 was driven at a rational speed of 10 to 80 rpm, the cylinder 12 fixed to the rotating table 14 was rotated. At the same time, the cylinder 12 was raised with the motor 18 at a speed of 10 to 80 mm/min depending upon the rotational speed of the ball screw 16 and the pitch of the ball screw 16.

At the same time, dry compressed air was supplied under a pressure of 1 to 3 kgf/cm$^2$ at a flow rate of 50 to 200 L/min from the air supply port 26 into the closed pressure vessel 11. The dry compressed air supplied into the closed pressure vessel 11 was passed through the through hole 28 having a diameter of 3 mm formed through the partition board 27 on which the nut 20 was fixed, and was then passed through the air passage 41 defined between the cylinder 12 and the suction nozzle 30 having a diameter of 20 mm. The cylindrical lower end portion 30b of the suction nozzle 30 projecting inside the closed pressure vessel 11 has a length of 113 mm. The suction nozzle 30 has the pipe 33 embedded therein and forming a tubular passage. The pipe 33 has an inner diameter of 3 mm and a length of 150 mm. The dry compressed air introduced into the cylinder 12 was sucked from the suction port 32 having a diameter of 6 mm into the tubular passage of the pipe 33, and was discharged from the discharge port 34 to the outside of the powder dispersing apparatus 10. As the cylinder 12 in rotation was raised in the closed pressure vessel 11, the powder 36 in the cylinder 12 was scraped off or up to float by means of the scraper blade 40a of the disk-shaped scraper 40 having a diameter of 21 mm. The scraper 40 was fixed to the lower end surface of the suction nozzle 30 with a space of 3 mm defined therebetween. The scraper blade 40a was formed by cutting the disk of the scraper 40 along the radius thereof and bending one of the adjacent cut portions by a distance of 0.5 to 1 mm from the other portion of the disk. The powder 36 scraped to float by the scraper blade 40a of the scraper 40 was sucked into the suction port 32 located just over the scraper blade 40a by the flow of the compressed air introduced from the air passage 41 between the cylinder 12 and the suction nozzle 30 into the suction port 32, thus being conveyed in the pipe 33. The powder 36 sucked with the air from the suction port 32 into the pipe 33 was sufficiently mixed and dispersed in the air during conveyance in the tubular passage of the pipe 33. Thus, the air containing the enough dispersed powder (the powder air mixture) was passed through the pipe 33 to the discharge port 34, and was then supplied to the outside of the powder dispersing apparatus 10 in a continuous fashion.

EXAMPLE 2

As shown in FIG. 4, the motor 46 for rotating the cylinder 12 and the motor 48 for vertically moving the cylinder 12 were independently set as the rotating means and the vertically moving means, respectively, in the powder dispersing apparatus 50. Further, the linear bearing 42 was provided between the closed pressure vessel 11 and the vertically movable member 44 to smoothly move the vertically movable member 44. The cylinder 12 was rotated at a high speed of 80 to 300 rpm by operating the rotation motor 46, and was simultaneously raised at a low speed of 0.1 to 10 mm/min by operating the vertical movement motor 48. The other process conditions were set similar to those in Example 1 to operate the powder dispersing apparatus 50. In the powder dispersing apparatus 50 shown in FIG. 4, the degree of dispersion and the concentration of dispersed powder could be more properly adjusted than those in the powder dispersing apparatus 10 shown in FIG. 1.

EXAMPLE 3

Figure 5:
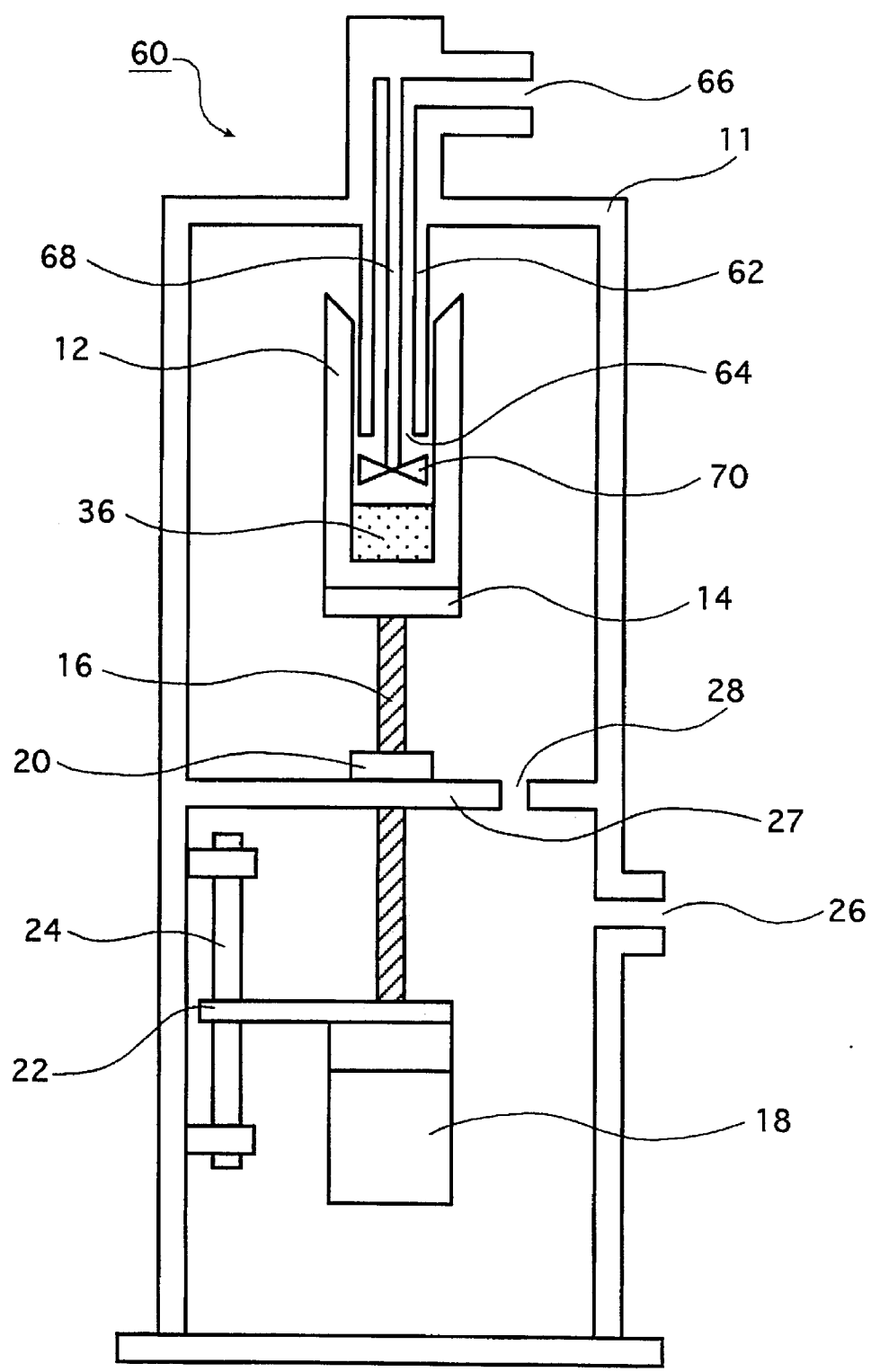

The powder dispersing apparatus 60 shown in FIG. 5 was used to disperse the powder 36 and obtain dispersed powder with various degrees of dispersion and concentrations.

The powder dispersing apparatus 60 was constructed by using the cylinder 12 having an inner diameter of 20 mm and a depth of 80 mm, the suction nozzle 62 having a diameter of 19 mm and a length of 90 mm at a portion projecting inside the closed pressure vessel 11, the suction port 64 having a diameter of 12 mm, the support rod 68 having a diameter of 6 mm, and the screw 70 having an outer diameter of 19 mm. The other parts and the process conditions of the powder dispersing apparatus 60 were made similar to those in Example 1.

In the powder dispersing apparatus 60, dry compressed air supplied from the air supply port 26 into the closed pressure vessel 11 was passed through the through hole 28 having a diameter of 3 mm formed through the partition board 27 to which the nut 20 was fixed, and through the air passage between the suction nozzle 62 and the cylinder 12 to reach the powder 36. Then, the dry compressed air was sucked from the suction port 64 into the air passage formed in the suction nozzle 62, and was discharged from the discharge port 66 to the outside of the powder dispersing apparatus 60. As the cylinder 12 in rotation was raised, the powder 36 in the cylinder 12 was gradually agitated and floated by the screw 70. The screw 70 having an outer diameter of 19 mm was mounted to the lower end of the support rod 68 having a diameter of 6 mm, which was fixed to the inner surface of the air passage defined in the suction nozzle 62 and was projected out of the suction port 64 of the suction nozzle 62, with a space of 5 mm defined between the suction nozzle 62 and the screw 70. The floating powder 36 agitated by the screw 70 was dispersed and mixed by the air flow introduced through the air passage between the cylinder 12 and the suction nozzle 62 into the cylinder 12. Then, the floating powder 36 thus dispersed and mixed was sucked from the suction port 64 of the suction nozzle 62 together with the compressed air into the air passage in the suction nozzle 62, and was then supplied from the discharge port 66 to the outside of the powder dispersing apparatus 60 in a continuous fashion.

EXAMPLE 4

Figure 6:
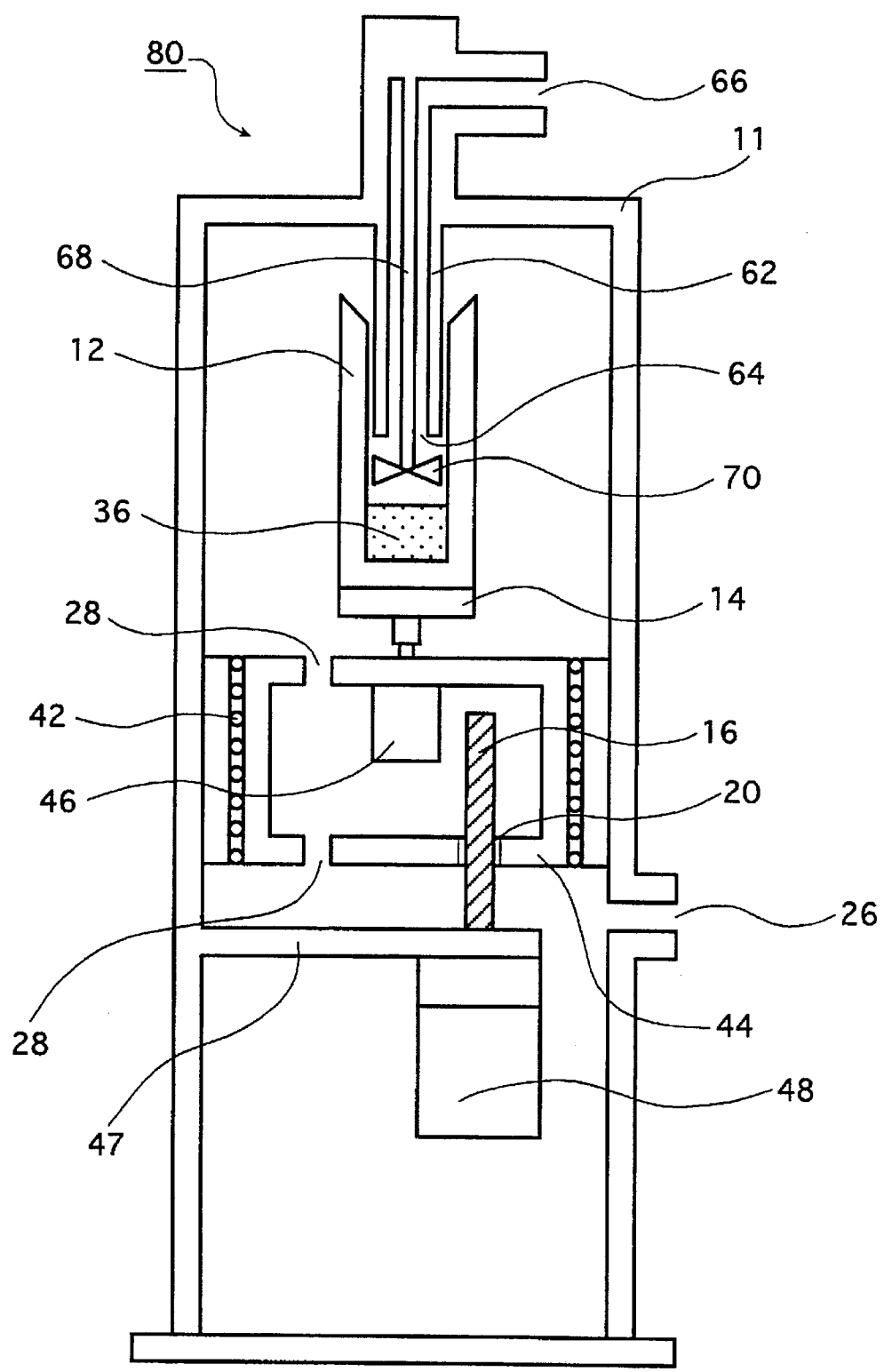

As shown in FIG. 6, the motor 46 for rotating the cylinder 12 and the motor 48 for vertically moving the cylinder 12 were independently set as the rotating means and the vertically moving means, respectively, in the powder dispersing apparatus 80 as similar to the powder dispersing apparatus 50 shown in FIG. 4. The conditions of rotation and rise of the cylinder 12 by the motors 46 and 48 were set similar to those in Example 2, and the other conditions were set similar to those in Example 3. In the powder dispersing apparatus 80 shown in FIG. 6, the degree of dispersion and the concentration of dispersed powder could be more properly adjusted than those in the powder dispersing apparatus 60 shown in FIG. 5.

As described above, in the powder dispersing apparatus of the present invention, the sample powder is stored in the powder storing member, and the dry compressed air is supplied from the air supply port into the closed pressure vessel. At the same time, the powder storing member is rotated and raised by the rotating means and the vertically moving means to thereby make the scraper blade of the scraper scrape up and float the sample powder. The supply of the dry compressed air into the closed pressure vessel produces a pressure difference between the pressure inside the closed pressure vessel and the pressure inside a powder measuring device or the like connected to the discharge port opening outside the closed pressure vessel. Owing to this pressure difference, the floating sample powder is sucked from the suction port of the suction nozzle into the tubular passage formed in the suction nozzle together with the dry compressed air introduced through the air passage defined between the outer side surface of the suction nozzle and the inner side surface of the powder storing member. During the conveyance of the powder and the air in the tubular passage, the powder is enough dispersed in the air. Thus, the powder air mixture obtained above is discharged from the discharge port of the tubular passage to the outside of the powder dispersing apparatus.

According to the powder dispersing apparatus of the present invention, even when the sample powder is small in amount, a given amount of powder can be scraped off or up to float. Further, since the powder is fed by the pressure difference, the dispersibility of the powder in the air passage, especially, in the tubular passage of the suction nozzle can be greatly improved. According to the powder dispersing apparatus of the present invention, the powder can be dispersed and mixed in a gas, especially, in the air always at a constant concentration because of no possibility of pulsation. Further, the amount of the floating powder, that is, the concentration of the powder gas mixture can be freely set by changing the moving speed of the powder storing member or the diameter or length of the air passage, especially, the tubular passage of the suction nozzle. According to the powder dispersing apparatus of the present invention, the floating powder can be generated simply by storing the powder into the powder storing member, supplying the dry compressed air into the closed pressure vessel, and rotating and raising the powder storing member by the rotating means and the vertically moving means. Thus, the operability can be improved. Additionally, it is unnecessary to wash the interior of the powder dispersing apparatus after operation, thus improving the maintainability, because the powder hardly remains in all parts of the closed pressure vessel except in the powder storing member after operation. Further, according to the present invention, the tubular passage is embedded in the suction nozzle, so that the suction nozzle can be easily mounted into and removed from the closed pressure vessel, thus improving the operability.

While the invention has been described with reference to specific embodiments, the description is illustrative and is not to be construed as limiting the scope of the invention. Various modifications and changes may occur to those skilled in the art without departing from the spirit and scope of the invention as defined by the appended claims.

What is claimed is:

1. A powder dispersing apparatus comprising:

a hollow closed pressure vessel having an air supply port;

a suction nozzle mounted to a top portion of said closed pressure vessel and having a cylindrical portion projecting into said closed pressure vessel, said suction nozzle being formed with a tubular passage having a suction port at a lower end of said cylindrical portion and a discharge port opening outside said closed pressure vessel;

a scraper fixed to said lower end of said cylindrical portion of said suction nozzle so as to be spaced a given distance therefrom, said scraper having a scraper blade located just under said suction port;

a powder storing member for storing powder, said powder storing member being mounted in said closed pressure vessel so as to be rotatable and vertically movable so that said scraper and said cylindrical portion of said suction nozzle are inserted in said powder storing member with a given space defined between an outer circumferential surface of said cylindrical portion of said suction nozzle and an inner circumferential surface of said powder storing member to form an annular air passage;

means for rotating said powder storing member; and means for vertically moving said powder storing member.

2. A powder dispersing apparatus according to claim 1, wherein said rotating means and said vertically moving means are provided in said closed pressure vessel.

3. A powder dispersing apparatus according to claim 1, wherein one pipe forming said tubular passage is embedded in said suction nozzle.

4. A powder dispersing apparatus according to claim 1, wherein at least two pipes each forming said tubular passage are embedded in said suction nozzle, one end of each pipe opening to said lower end of said cylindrical portion of said suction nozzle to form said suction port, the other ends of all said at least two pipes being joined together to form said discharge port.

5. A powder dispersing apparatus according to claim 1, wherein said rotating means and said vertically moving means comprise a nut fixed to a partition board in said closed pressure vessel, a vertically movable ball screw engaged with internal threads of said nut, a motor for rotating said ball screw, a rotation stop to which said motor is fixed, and a motor guide fixed to an inner wall surface of said closed pressure vessel so as to extend in parallel to an axis of said ball screw, for vertically slidably engaging said rotation stop, whereby said motor is driven to rotate and vertically move said powder storing member fixed to an upper end of said ball screw.

6. A powder dispersing apparatus according to claim 1, wherein said vertically moving means comprises a vertical movement motor fixed to a partition board in said closed pressure vessel, a ball screw adapted to be rotated by said vertical movement motor, a vertically movable member having an internal thread portion engaged with said ball screw, and a linear bearing fixed to an inner wall surface of said closed pressure vessel for vertically movably supporting said vertically movable member; and said rotating means comprises a rotation motor fixed to said vertically movable member, and a rotating shaft adapted to be rotated by said rotation motor and having an upper end fixed to said powder storing member.

7. A powder dispersing apparatus comprising:

a hollow closed pressure vessel having an air supply port and a discharge port;

a powder storing member provided in said closed pressure vessel for storing powder;

a suction nozzle communicating with said discharge port of said closed pressure vessel and inserted in said powder storing member with a given space defined between an outer circumferential surface of said suction nozzle and an inner circumferential surface of said powder storing member to form an annular air passage;

an agitator provided so as to be spaced from a lower end of said suction nozzle;

means for rotating one of said agitator and said powder storing member relative to each other; and means for vertically moving one of said agitator and said powder storing member relative to each other.

8. A powder dispersing apparatus according to claim 7, wherein said agitator and said suction nozzle are fixed to said closed pressure vessel, and said rotating means and said vertically moving means are stored in said closed pressure vessel to rotate and vertically move said powder storing member.

* * * * *